United States Patent [19]
Krivitski

[11] Patent Number: 6,061,590
[45] Date of Patent: May 9, 2000

[54] METHOD AND APPARATUS FOR PREDICTING INTRADIALYTIC MORBID EVENTS THROUGH THE MONITORING OF A CENTRAL BLOOD VOLUME

[75] Inventor: Nikolai M. Krivitski, Ithaca, N.Y.

[73] Assignee: Transonic Systems, Inc., Ithaca, N.Y.

[21] Appl. No.: 08/868,283

[22] Filed: Jun. 3, 1997

[51] Int. Cl.$^7$ ...................................................... A61B 6/00
[52] U.S. Cl. .......................... 600/431; 600/481; 600/504; 600/526
[58] Field of Search ..................................... 600/481, 483, 600/486, 507, 454, 465, 468, 479, 431, 504, 526

[56] References Cited

U.S. PATENT DOCUMENTS

| | | | |
|---|---|---|---|
| 5,230,341 | 7/1993 | Polaschegg | 600/481 |
| 5,331,958 | 7/1994 | Oppenheimer | 600/322 |
| 5,453,576 | 9/1995 | Krivitski | 600/481 |
| 5,595,182 | 1/1997 | Krivitski | 600/505 |
| 5,601,080 | 2/1997 | Oppenheimer | 600/322 |
| 5,687,726 | 11/1997 | Hoeft | 600/431 |

OTHER PUBLICATIONS

Abstracts XXXII Congress of the International Union of Physiological Sciences Aug. 1st–6th, Glasgow, 1.
Journal of the American Society of Nephrology; Sep. 1993; vol. 4, No. 3; "Dialysis", p. 357; Published by Williams & Wilkins.
ASAIO Journal 1992; Slide Forum 4, Hemodialysis/Blood Volume and Flow; "Continuous Measurement of Blood Volume During the Hemodialysis by an Optical Method"; pp. M181–M185; De Vries et al.
ASAIO Journal 1994; Poster Session–Renal 2; Hematocrit as an Indicator of Blood Volume and a Predictor of Intradialytic Morbid Events; pp. M691–M696; Steuer et al.

*Primary Examiner*—Cary O'Connor
*Assistant Examiner*—Navin Natnithithadha
*Attorney, Agent, or Firm*—Harter, Secrest & Emery LLP; Brian B. Shaw, Esq.; Stephen B. Salai, Esq.

[57] ABSTRACT

A method and apparatus for identifying a central blood volume and monitoring changes in the central blood volume during hemodialysis to assist in predicting an onset of intradialytic morbid events. A method of determining a central blood volume mean transit time in a patient system having the central volume and a tubing portion includes measuring a system mean transit time through the tubing portion and the central volume; calculating a tubing portion mean transit time corresponding to passage of an indicator through the tubing portion; adjusting the measured system mean transit time in response to the calculated tubing portion mean transit time to produce the central volume mean transit time and calculating a central volume by multiplying the central volume mean transit time by the cardiac output. This technology can be used not only in hemodialysis, but in intensive care units or during the surgery with extracorporeal circulation systems.

27 Claims, 4 Drawing Sheets

METHOD AND APPARATUS FOR PREDICTING INTRADIALYTIC MORBID EVENTS THROUGH THE MONITORING OF A CENTRAL BLOOD VOLUME

The present application is by Nikolai M. Krivitski as the inventor, which application is assigned to Transonic Systems Inc. of Ithaca, N.Y.

FIELD OF THE INVENTION

The present invention generally relates to complications arising during medical procedures that may alter blood composition, and to a method and apparatus for assisting in the prediction of intradialytic morbid events often associated with hemodialysis, intensive care unit treatments and surgery. More particularly, the present invention generally relates to the measurement of hemodynamic parameters by indicator dilution, and specifically to monitoring changes in a central blood volume to predict morbid events through the measurement of dilution effects of an indicator in the bloodstream of a patient.

BACKGROUND OF THE INVENTION

In a large number of medical procedures, it is important to monitor hemodynamic parameters in a patient. For example, in procedures such as hemodialysis, a filter is used to remove selected particles and liquids from the bloodstream of a patient, but if the particles and liquids are removed too quickly, the vascular system of the patient may collapse.

Thus, the treatment of patients by hemodialysis is frequently accompanied by acute symptoms or complications such as hypotension, severe muscular cramps and lightheadedness. Although the pathophysiology of intradialytic morbid events (IME) is complex and multifactoral, hypovolemia has been suggested to play a triggering role.

Intravascular volume depletion results from an imbalance between the rates of extra corporeal ultrafiltration and refilling the blood compartment. As red cell volume remains essentially constant during hemodialysis, changes in hematocrit (R. R. Steuer et al., Hematocrit as an Indicator of Blood Volume and a Predictor of Intradialytic Morbid Events, ASAIO J., 1994, 38: M181–M185); hemoglobin (M de Vries et al., Continuos Measurement of Blood Volume During Hemodialysis by an Optical Method, ASAIO J., 1992, 38: M181–M185); and ultrasound velocity (U.S. Pat. No. 5,230,341 to Polashegg) have been traditionally viewed as inversely related to changes in the circulating blood volume. This relationship has been used in attempts to project dialysis induced hypotension.

Existing technology for monitoring total blood volume in a patient during hemodialysis relies upon the assumption that changes in volume are inversely proportional to an arterial concentration of large blood particles, such as hematocrit, hemoglobin, or total proteins that cannot defuse through the dialysis membranes. However, it is known that arterial hematocrit alone does not represent whole blood volume concentration. In the capillaries, arterioles and venule hematocrit may be less than half the arterial concentration. (Gibson J G, et al. The Distribution Of Red Cell And Plasma In Large And Minute Vessels Of The Normal Dog, Determined By Radioactive Isotopes Of Iron And Iodine, J. Clin. Invest. 25:848, 1946). Therefore, observed changes in hematocrit (hemoglobin) may not relate to the actual volume changes but to the redistribution of red cells in the vascular space. Thus, the present technologies may not measure total blood volume changes accurately.

In the Abstract by Jacobson S H, et al., (Double Indicator Dilution Estimation of Extravascular Lung Water and Cardiac Output During Hemodialysis, Journal of American Society of Nephrology, Vol. 4, No. 3, Abstract, p.357, 1993), the blood volume that is located in the right heart, lungs and left heart was measured by injecting dye into a venous port and recording dilution curves during the blood withdraw through an arterial port into a dencitometer. This approach fails to accommodate the significant amount of time that the indicator travels in extracorporeal tubing. Thus, this measurement may not provide a sufficiently reliable measurement for diagnosis of IME. These reliability issues also exist when the measurements are performed with intravenous injections in a venous catheter and the dilution curve is recorded on an extracorporeal tubing system that withdraws blood from an artery.

Therefore, the need exists for a method and apparatus for assisting the prediction of an onset of IME during procedures such as hemodialysis. The need also exists for the identification and monitoring of a physiological parameter which can assist in the prediction of complications during hemodialysis, intensive care unit treatments and surgical procedures.

SUMMARY OF THE INVENTION

The present invention employs an identification and monitoring of a central blood volume to assist in predicting the onset of IME, and particularly during hemodialysis. This technology can be used not only in hemodialysis, but in intensive care units or during surgery with extracorporeal circulation systems.

The present method monitors the central blood volume substantially independent of the associated extracorporeal tubing which may be employed in a monitoring or hemodialysis system. The present invention employs a method and apparatus for measuring blood parameters by dilution, wherein an indicator such as a saline solution is injected into a bloodstream and its downstream effects are measured by parameters such as the velocity of ultrasound in the bloodstream.

The present invention encompasses a method of determining and monitoring the central blood volume in a circulation system, wherein the circulation system includes the central blood volume and a tubing portion which may include an extra corporeal portion. The present method includes introducing an indicator bolus into a venous portion of the circulation system; identifying an indicator curve (dilution curve) in the arterial side of the tubing portion; measuring a system mean transit time of the indicator bolus through the tubing portion and the central blood volume; calculating a mean transit time of the indicator bolus through the tubing portion; adjusting the measured system mean transit time in response to the calculated mean transit time and an indicator dilution curve to obtain a central blood volume mean transit time and determining the central blood volume.

The apparatus for calculating and monitoring a change in the central blood volume includes a dilution sensor such as a sound velocity sensor coupled to at least an arterial portion of a blood system for detecting a dilution of the blood, a blood flow sensor for measuring the blood flow rate; an injection port in the circulation system; an indicator injectable through the injection port to produce an indicator bolus; and an evaluating device configured to determine a mean transit time in the tubing portion and a system mean transit time to identify a mean transit time through the central volume.

DETAILED DESCRIPTION OF THE PREFERRED EMBODIMENTS

Figure 1:
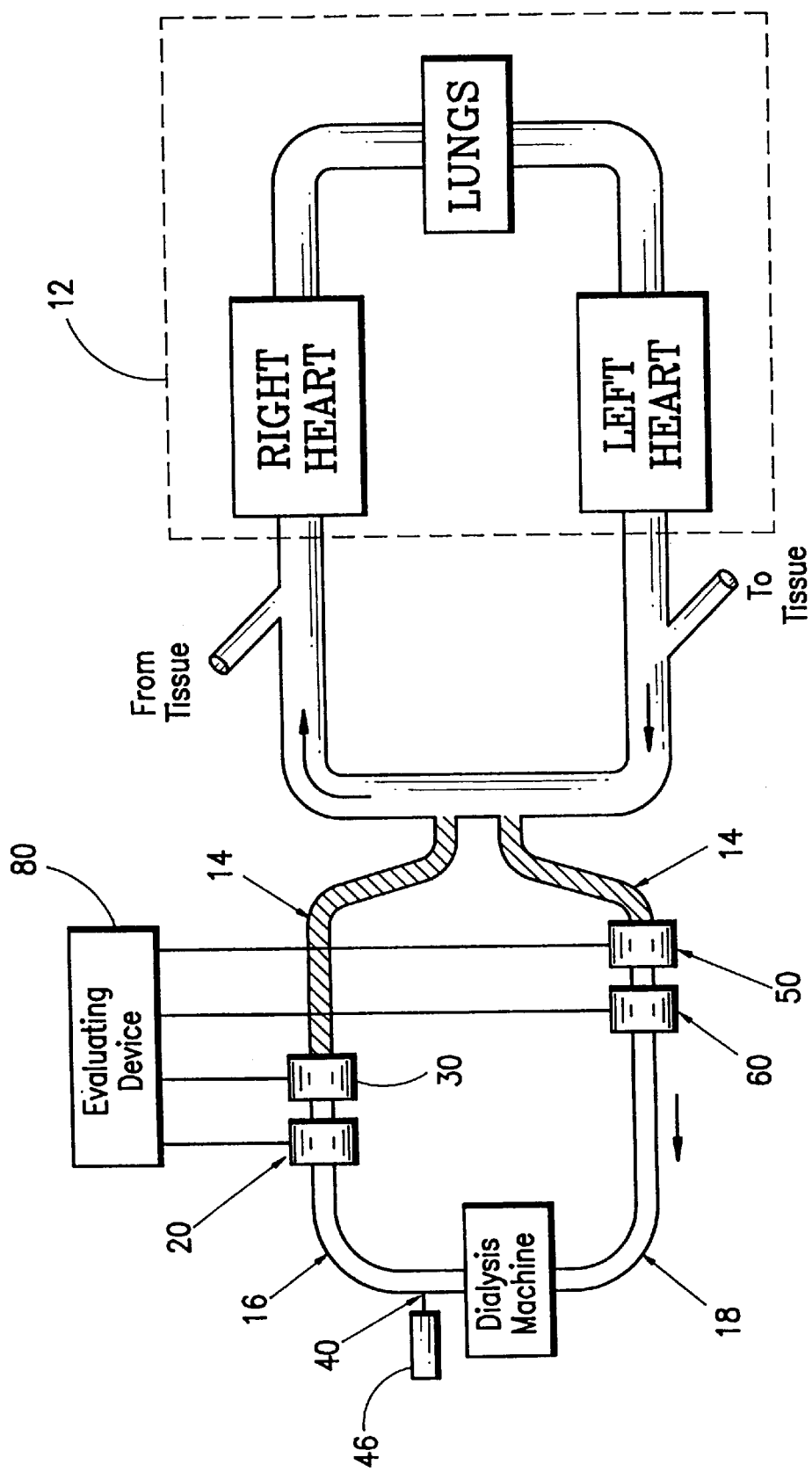
FIG. 1 is a schematic diagram showing a hemodialysis circulating system connected to a cardiovascular system with vascular access.

Referring to FIG. 1, a schematic diagram showing a hemodialysis circulating system 6 connected to a cardiovascular system 8 with vascular access and the accompanying hardware is shown. U.S. Pat. No. 5,453,576 (N. Krivitski) is hereby expressly incorporated by reference.

The Apparatus

The apparatus for calculating and monitoring a change in a central blood volume 12 includes a venous dilution sensor 20; a venous flow rate sensor 30; an injection port 40 in the circulation system; an injectable indicator 46; an arterial dilution sensor 50; an arterial flow rate sensor 60; and an evaluating device 80. As discussed, the invention may be practiced with a single dilution sensor and flow rate sensor in conjunction with the evaluating device. However, for purposes of description, the system is set forth with both arterial and venous dilution sensors 50 and 20.

A circulation system includes the central blood volume 12 and a tubing portion 14. As used herein, the term "central blood volume 12" includes the right heart, the lungs and the left heart, as well as the vascular structure connecting the right heart to the lungs, the lungs to the left heart and some portion of the aorta and large veins located between the artificial system and the right and left heart. That is, in theory the central blood volume 12 would include only the right heart, the lungs, the left heart and the vascular structure directly connecting the right heart to the lungs and the lungs to the left heart. However, in practice it is impracticable to introduce a dilution indicator 46 immediately adjacent the large vein at the right heart, or locate the arterial dilution sensor 50 immediately adjacent the aorta at the left heart. Therefore, the central blood volume 12 often includes a limited length of the vein entering the right heart and the aorta exiting the left heart. The tubing potion 14 is defined as that portion of the circulation system that does not lie within the central blood volume 12. The tubing portion 14 may include external, extra corporeal lines within the patient, but that lie outside the central blood volume 12. The tubing portion 14 is shown in shading in FIGS. 1, 4 and 5.

The evaluating device 80 may be personal computer capable of curve plotting and performing the calculations set forth in the present application. The evaluating device 80 receives signals from the sensors 20, 30, 50 and 60 and generates values representing flow rates and volumes and is capable of determining a mean transit time in the tubing portion and a system mean transit time to identify a mean transit time through the central volume 12.

The venous and arterial dilution sensors 20 and 50 detect a blood parameter, and particularly variations of a blood parameter. Ultrasound velocity sensors as well as temperature sensors and optical sensors, density or electrical impedance sensors may be used to detect changes in blood parameters. It is understood that other sensors that can detect blood property changes may be employed. The operating parameters of the particular system will substantially dictate the specific design characteristics of the dilution sensor, such as the particular sound velocity sensor. The venous and arterial dilution sensors 20 and 50 may be identical components. The venous and arterial dilution sensors 20 and 50 are operably connected to the evaluating device 80. The dilution sensors 20 and 50 may be sound velocity sensors and any of a variety of readily available commercial devices, such as HD01 Hemodialysis monitor manufactured by Transonic Systems Inc. Ithaca N.Y. A dilution sensor 50 is coupled to at least an arterial portion 18 of a blood system for detecting the dilution of the blood, identifying a dilution curve. Preferably, the arterial dilution sensor 50 is operably connected to the arterial line 18 and the venous dilution sensor 20 is operably connected to the venous line 16. Ultrasonic sensors measure sound velocity dilution as the indicator 46 is carried past the sensor by the bloodstream, and changes in sound velocity are plotted to permit calculation of various blood parameters. The time at which the indicator 46 reaches the sensor 50 after injection, the area under the plotted curve representing the changes in sound velocity at the sensor, and the amplitude of the measurement all provide information concerning the blood characteristics.

The injection port 40 is located in the circulation system to allow selective vascular access to the blood flow. The injection port 40 may be any of a variety of constructions allowing single or repeated access to the blood flow. For example, indicator 46 may be introduced into arterial injection port before the hemodialysis filter, it may be introduced into the filter or it may be introduced into the venous line 16 after the filter. The injection port 40 may be located at any point along the circulating system. For example, during intensive care treatment or procedures and surgery, the injection port may be an intravenous catheter 36.

The injectable indicator 46 may be any of the known indicators including saline solution or any other solution that changes blood properties that can be detected by dilution sensors. The injectable indicator 46 may be introduction of temperature gradient or another blood property changes without introduction additional volume or other blood parameter. Preferably, the indicator 46 is injectable through the injection port 40 and is non toxic with respect to the patient and non reactive with the material of the system. The injected indicator 46 thus forms an indicator bolus.

The flow sensors 30 and 60 measure the flow rate in the local section of the circulation system. The arterial and venous flow rate sensors 60 and 30 provide output signals corresponding to blood flow measurement. Each of the blood flow sensors 30 and 60 may be a Bypass Flow Meter model HT 109 or model T106 produced by Transonic Systems, Inc., Ithaca, N.Y., for example.

Figure 3:
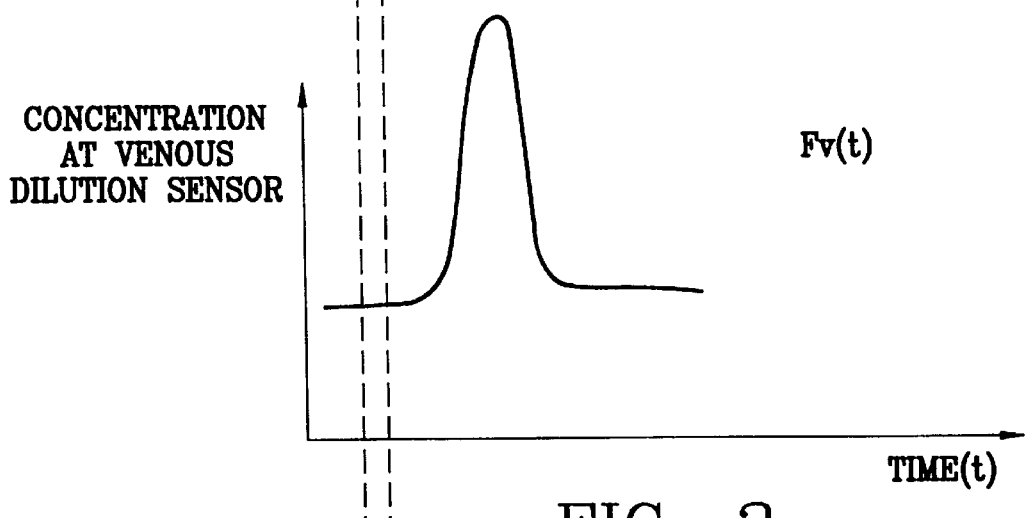
FIG. 3 is a dilution (indicator) curve recorded by a venous dilution sensor.

For injections through the catheter 36, a timing sensor 38 that records the timing of the injection may be a sensor that records the beginning and the end of the injection. The timing sensor 38 may be a flow sensor or a sensor for measuring a blood property, such as a sound velocity or temperature sensor may function as the timing sensor 38 to record the timing of the injection. The timing of the catheter injection that is very short may be recorded by manually activating a switch 82 that is on or operably connected to the evaluating device 80 at the moment of injection. Thus, the time of injection can be recorded. Further, the time of injection may be defined by an initiation of the injection and a termination of the injection, thereby providing an injection time window, as shown in FIG. 3.

Figure 2:
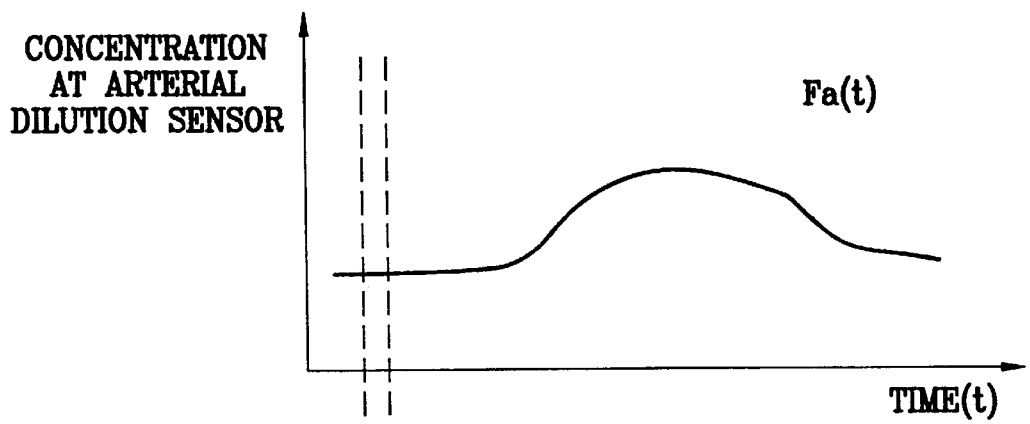
FIG. 2 is a dilution (indicator) curve recorded by an arterial dilution sensor.

The velocity of ultrasound in blood is a function of, among other things, the proteins and ions contained in the blood, with the sound velocity increasing with an increase in protein concentration. Accordingly, the velocity of sound through a blood sample can be varied by diluting the blood with an indicator 46 having different acoustical characteristics than those of the blood; for example, through the use of a saline solution that has no proteins. By injecting such an indicator 46 into a known blood flow, the diluting effect of the indicator over a period of time can be accurately determined by the sound velocity sensor which is responsive to changes of sound velocity in the blood. In one embodiment, the sound velocity sensor is disposed in the venous portion 16 of the circulation system, downstream of the injection port 40, so that the indicator 46 passes the sound velocity sensor, with the measured diluting effect being used to determine the corresponding dilution curve (indicator curve), as shown in FIG. 2.

The dilution measurements can be made in an extracorporeal portion of the circulation blood system in which clamp-on sound velocity sensors are secured for example, to tubing leading to exterior blood treatment equipment such as a hemodialysis machine, or the like as shown in FIG. 1. In such an embodiment, referred to herein as a clamp-on measurement system, measurements of blood are made outside the patient's body; for example, in extra corporeal tubing leading from the vascular system of the patient to a blood treatment system such as a dialysis machine. In such a system, blood is drawn from the patient, passed through suitable tubing to a dialysis filter and is then returned through tubing to the patient, usually to the same vessel from which the blood being treated was initially drawn, but downstream of the withdrawal site. Clamp-on sensors 30 and 60 such as ultrasonic flow meters manufactured by Transonic Systems of Ithaca N.Y. are suitable for measuring blood flow through the tubing. However, the measured parameters are functions not only of blood characteristics, but of tube material and geometry. Alternatively, the sensors may be located inside the body at the injection catheter or other internal site.

The Method

Figure 4:
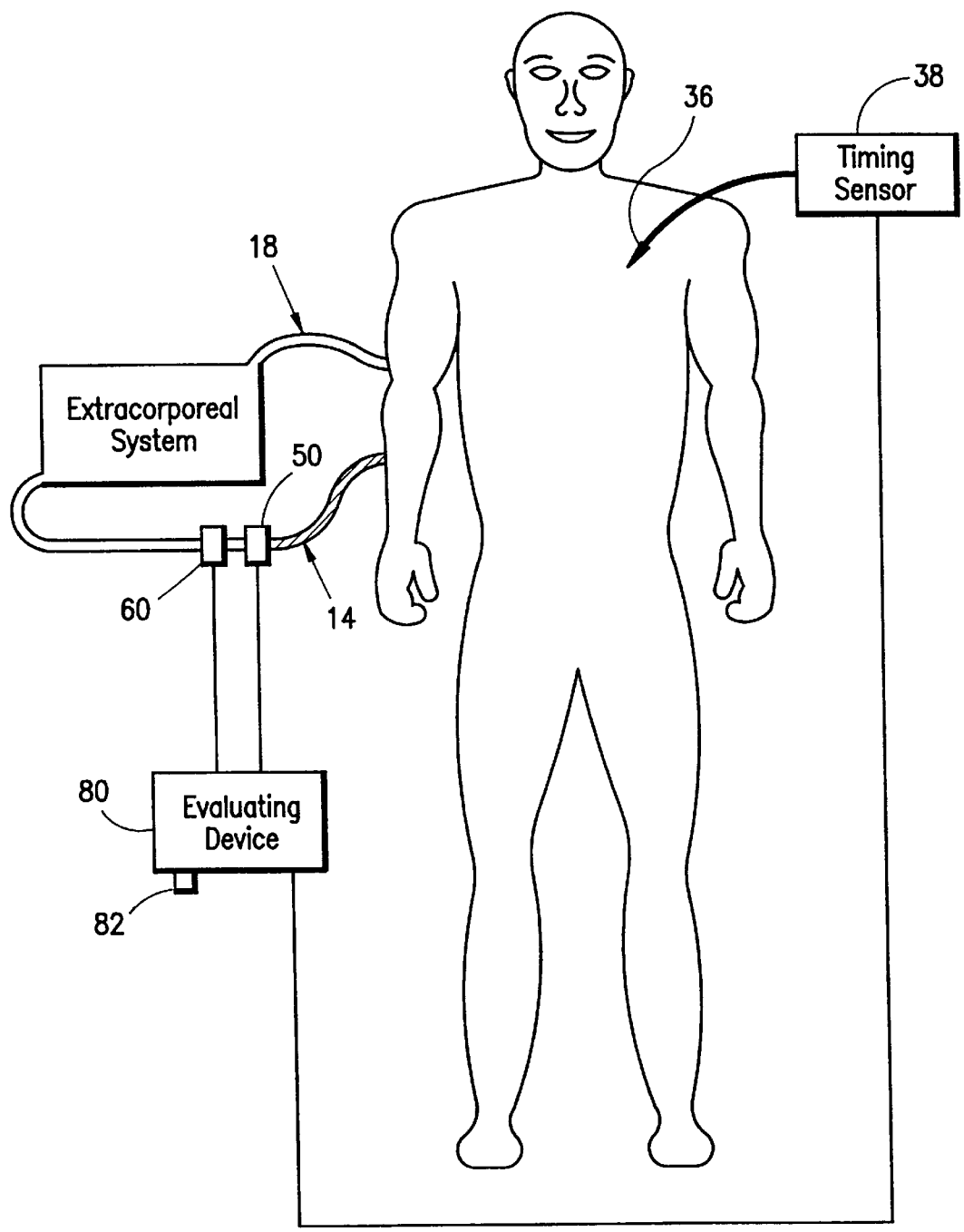
FIG. 4 is a schematic diagram showing an extracorporeal system connected to a cardiovascular system of the patient.
Figure 5:
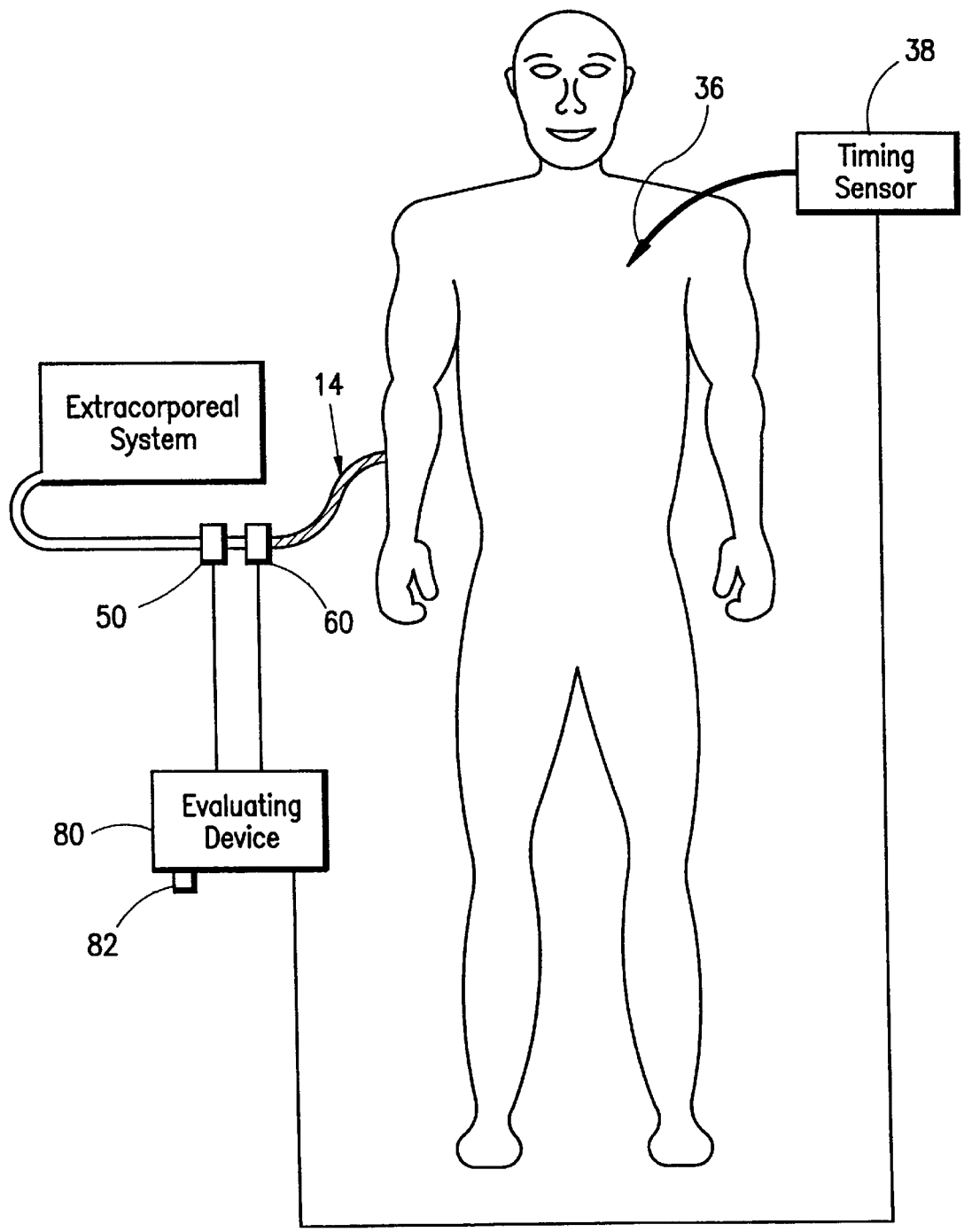
FIG. 5 is a schematic diagram showing an alternative extracorporeal system connected to a cardiovascular system of the patient.

To determine the central blood volume 12 through dilution technology and specifically sound velocity, the indicator 46 bolus is injected through the injection port 40. Although the specific parameters of the bolus are sensitive to and may be dictated by the particular operating environment, a 30 ml bolus of isotonic saline at 37° C. is injected into the venous line 16, as shown in FIG. 3. It is understood the indicator 46 may be introduced at any place in the circulating system as shown in FIGS. 4 and 5, or the hemodialysis circulating system.

Generally, the central volume 12 is obtained by multiplying the cardiac output by the central volume mean transit time:

$$MTT_a = \frac{\int F_a(t) t \, dt}{\int F_a(t) dt} \quad \text{(Equation 2)}$$

where CO is the cardiac output, and $F_a(t)$ is the dilution curve recorded in the arterial portion of the circulation system after intravenous injection, as shown in FIG. 2.

To address the problem of tubing influence, additional measurements are performed and another formula employed. Specifically, a mean transit time of the indictor bolus 46 through the tubing portion 14 is based upon a calculated volume of the tubing portion and the flow rate through the tubing portion.

$$CBV = CO\left(MTT_a - MTT_v - \left(\frac{V_a}{Q_{ba}} + \frac{V_b}{Q_{bv}}\right)\right), \quad \text{(Equation 3)}$$

where $MTT_a$ and $MTT_v$—mean transit time of the indicator 46 recorded by the arterial sensor curve Fa(t) and venous sensor curve Fv(t), respectively.

$$MTT_a = \frac{\int F_a(t) t \, dt}{\int F_a(t) dt} \quad \text{(Equation 4)}$$

$$MTT_v = \frac{\int F_v(t) t \, dt}{\int F_v(t) dt} \quad \text{(Equation 5)}$$

$$CO = Q_{ba}\left(\frac{\int F_v(t) dt}{\int F_a(t) dt}\right) \quad \text{(Equation 6)}$$

In these equations, $V_a$ and $V_b$ represent the arterial and venous tubing volumes respectively; and $Q_{ba}$ and $Q_{bv}$ represent the arterial and venous tubing blood flow, respectively.

For injection through an intravenous catheter 36 and recording by the dilution sensor in extracorporeal tubing system 14 connected to the vascular system, Equation 3 will be rewritten:

$$CBV = CO\left(MTT_a - \left(\frac{V_a}{Q_{ba}}\right)\right), \quad \text{(Equation 7)}$$

In equations 3–6, the time of integration of all the integrals should start at the beginning of the venous bolus or at the moment of injection, if available. For equation 7, the time of integration of all integrals should start at the moment of injection when the indicator 46 starts moving into the vascular system. Hence, the desirability of a timing sensor or manual activation of the start time input into the evaluating device 80.

If only a single dilution sensor 50 is employed, then it is necessary to determine the moment of injection of the venous bolus injection. The recording of this injection moment may be accomplished through the timing 38 sensor or the manual activation, such as the switch 82 on the evaluating device 80. Then relevant integral then begins at the injection moment and extends to the passage of the bolus.

Alternatively, if a venous and an arterial dilution sensor 20 and 50 are employed, then it is not required to record the injection moment. In the two sensor configuration, the time between passage of the bolus between the sensors is recorded, as this time is independent of the actual injection moment, it is not necessary to record the injection moment. However, the elapsed transit time from the venous dilution sensor 20 to the arterial dilution sensor 50 is recorded.

After injecting an isotonic saline venous dilution indicator 46, the venous dilution sensor 20 (sound velocity sensor)

will identify and record a dilution curve ($F_v(t)$). The mean transit time of the incoming bolus, $MTT_V$, is calculated via Equation 5. This measured $MTT_V$ helps eliminate the influence of the length of injection and volume between the injection port 40 and the venous dilution sensor 20. Simultaneously, the venous flow sensor 30 measures blood flow in venous line ($Q_{bv}$) to eliminate the influence of blood volume ($V_v$) in the tubing portion 14 between the venous dilution sensor 20 and the patient ($V_v$-previously measured). A corresponding signal is sent to the evaluating device 80. After the bolus travails right heart, lungs, left heart and enters the arterial line 18, the arterial dilution sensor 50 records dilution curve $F_a(t)$; using this curve, the evaluating device 80 calculates the cardiac output CO via Equation 6 and $MTT_a$ from Equation 4. The arterial blood flow sensor 60 measures arterial blood flow ($Q_{ba}$) to eliminate the influence of blood volume ($V_a$) in the tubing portion between the arterial sensor 50 and the patient ($V_a$-previously measured) and sends a corresponding signal to the evaluating device 80. The evaluating device 80 then calculates central blood volume 12 (CBV) via Equation 3.

The cardiac output CO can then be calculated according Equation 5, where $Q_{bv}$ is flow in the venous line 16 during the indicator 46 injection; $\int F_v(t)dt$ and $\int F_A(t)dt$ are the areas under the respective dilution (indicator) curves of the recorded by venous and arterial dilution sensors, 20 and 50 respectively. It is understood the transit times of equations 2, 4 or 5 and the cardiac output may be measured and calculated by a variety of different formulas. Such calculation does not preclude the application of the present invention and its adjustment for the tubing transit time in the calculation and monitoring of the central blood volume 12.

Although the present invention has been described in terms of particular embodiments, it is not limited to these embodiments. Alternative embodiments or modifications which would be encompassed by the invention may be made by those skilled in the art, particularly in light of the foregoing teachings. Alternative embodiments, modifications or equivalents may be included in the spirit and scope of the invention, as defined by the claim. For example, if the blood flow in the arterial line 18 and venous line 16 are the same, that is, ($Q_{ba}=Q_{bv}$), then only one sensor for blood flow in circulation system is needed. If the portion of tubing volume $V_a$ and $V_b$ is negligible, then only CO, $MTT_a$ and $MTT_v$ (see Equation 1) is required.

In addition, $$\frac{V_a}{Q_{ba}}, \frac{V_v}{Q_{bv}}$$

or $MTT_v$ may be calculated by a variety of methods. In fact, to eliminate the use of the flow sensor (shown in FIGS. 1, 4 and 5), the values may be approximated by a predetermined constant average value from prior experience, such as $$\frac{V_a}{Q_{ba}} = 1.3 \text{ seconds.}$$

If injections are made through the intravenous catheter 36 and the dilution curves are recorded in the extracorporeal circulation system including tubing portion 14 (Equation 7), then the only adjustment is needed in the arterial part of the system FIG. 4. This may be used not only in hemodialysis, but in intensive care units or during the surgery.

Further, referring to FIGS. 4 and 5, the extracorporeal system may include a circulation or merely a withdrawal of blood and reintroduction. Such extracorporeal systems are know in the art.

Thus, the adjustment for the tubing portion 14 volume may be accomplished by calculation or actual measurement, or approximately from experience and a constant average value is employed.

What is claimed is:

1. A method of determining a vascular central volume in a blood circulation system encompassing the vascular central volume and a tubing portion, comprising:
    (a) introducing a dilution indicator into the blood circulation system;
    (b) identifying a venous dilution curve corresponding to passage of the dilution indicator before the dilution indicator passes through the vascular central volume;
    (c) identifying an arterial dilution curve corresponding to passage of the dilution indicator after the dilution indicator has entered the vascular central volume;
    (d) measuring a system mean transit time of the dilution indicator through the tubing portion and the vascular central volume;
    (e) determining a mean transit time of the dilution indicator through the tubing portion;
    (f) adjusting the measured system mean transit time in response to the determined mean transit time and the venous dilution curve to obtain a central volume mean transit time;
    (g) calculating a cardiac output; and
    (h) determining the vascular central volume in response to the central volume mean transit time and cardiac output.

2. The method of claim 1, wherein determining the mean transit time in the tubing portion includes identify a tubing portion volume and a tubing portion flow rate.

3. The method of claim 1, wherein introducing the dilution indicator includes introducing a bolus into a venous side of the tubing portion.

4. The method of claim 1, wherein introducing the dilution indicator includes introducing a bolus into an arterial side of the tubing portion.

5. The method of claim 1, wherein introducing the dilution indicator includes introducing a bolus into a dialyzer portion of a circulating system.

6. The method of claim 1, wherein determining the vascular central volume includes multiplying the vascular central volume mean transit time by a cardiac output.

7. The method of claim 1, wherein measuring a system mean transit time of the dilution indicator through the tubing portion and the vascular central volume includes identifying a venous indicator curve in the blood circulation system on a venous side and an arterial indicator curve in the blood circulation system on an arterial side of the vascular central volume.

8. The method of claim 1, further comprising measuring the system mean transit time on a periodic basis.

9. The method of claim 8, further comprising determining the vascular central volume in response to measuring the system mean transit time on a periodic basis.

10. The method of claim 1, further comprising measuring a tubing blood volume between locations of the identifying an arterial indicator curve and identifying a venous indicator curve, and the vascular central volume.

11. The method of claim 1, wherein identifying a venous indicator curve corresponding to the introduction of the dilution indicator before passing through the vascular central volume includes recording the venous indicator curve.

12. The method of claim 1, wherein identifying an arterial indicator curve corresponding to the introduction of the dilution indicator after entering the vascular central volume includes recording the arterial indicator curve.

13. A method of determining a central volume mean transit time in a patient system having a central volume and a tubing portion, comprising:
(a) measuring a system mean transit time through the tubing portion and the central volume;
(b) calculating a tubing portion mean transit time corresponding to passage of an indicator through the tubing portion; and
(c) adjusting the measured system mean transit time in response to the calculated tubing portion mean transit time to produce the central volume mean transit time.

14. The method of claim 13, further comprising calculating a central volume based upon the central volume mean transit time.

15. The method of claim 13, multiplying the adjusted mean transit time by a cardiac output to obtain a central volume.

16. A method of enhancing prediction of an intradialytic morbid event resulting from hemodialysis through monitoring a physiological parameter, comprising:
(a) determining a central volume of blood in a patient during hemodialysis; and
(b) comparing during hemodialysis the determined central volume of blood to a previously determined central volume to identify a change in the central volume of blood.

17. The method of claim 16, further comprising comparing the change in the central volume of blood to a threshold value to predict an onset of the intradialytic morbid event.

18. The method of claim 16, wherein monitoring the central volume of blood is conducted by monitoring an indicator introduced into a patient circuit.

19. A method of determining a central volume in a system having the central volume and a tubing portion, comprising:
(a) introducing an indicator bolus into a venous portion of the system;
(b) identifying an indicator curve corresponding to the passage of the indicator bolus in an arterial portion of the system;
(c) measuring a system mean transit time of the indicator bolus through the tubing portion and the central volume;
(d) calculating a mean transit time of the indicator bolus through the tubing portion;
(e) adjusting the measured system mean transit time in response to the calculated mean transit time and the indicator curve to obtain a central volume mean transit time; and
(f) determining the central volume in response to the central volume mean transit time.

20. A method of determining a central volume mean transit time in a blood circulation system encompassing vascular central volume, comprising:
(a) introducing a dilution indicator into a venous portion of the blood circulation system;
(b) identifying an arterial dilution curve corresponding to passage of the dilution indicator in an arterial portion of the blood circulation system after at least a portion of the dilution indicator passing through the vascular central volume;
(c) measuring a system mean transit time of the dilution indicator through the vascular central volume; and
(d) adjusting the measured system mean transit time in response to the venous dilution curve to obtain a central volume mean transit time.

21. The method of claim 20, further comprising:
(a) calculating a cardiac output; and
(b) determining the vascular central volume in response to the central volume mean transit time and cardiac output.

22. An apparatus for determining a vascular central volume in a blood circulation system encompassing the central volume and a tubing portion, comprising:
(a) an arterial dilution sensor located along an arterial section of the blood circulation system;
(b) a flow sensor located along the blood circulation system; and
(c) an evaluating device operably connected to the arterial dilution sensor and the flow sensor, the evaluating device configured to determine a system mean transit time through the tubing portion and the central volume in response to a signal from the arterial dilution sensor, and adjust the measured system mean transit time in response to a calculated tubing portion mean transit time to produce the central volume mean transit time and determine the central volume by multiplying the central volume mean transit time by a cardiac output.

23. The apparatus of claim 22, wherein the flow sensor is located in an arterial section of the blood circulation system.

24. The apparatus of claim 22, wherein the flow sensor is located in a venous section of the blood circulation system.

25. The apparatus of claim 22, further comprising:
(a) a venous dilution sensor operably connected to the evaluating device; and
(b) a second flow sensor in one of the arterial section and the venous sections, the flow sensor being disposed in a remaining of the arterial section and the venous section.

26. The apparatus of claim 22, wherein the arterial dilution sensor is one of a thermal, sonic, ultrasonic, salinity, conductivity or impedance sensor.

27. The apparatus of claim 22, further comprising a timer for measuring the introduction of a dilution indicator.

* * * * *